United States Patent
Hausch et al.

(10) Patent No.: US 11,110,285 B2
(45) Date of Patent: Sep. 7, 2021

(54) ELECTRICAL FEEDTHROUGH WITH A SINTERED ELECTRICAL CONNECTION

(71) Applicant: Heraeus Deutschland GmbH & Co. KG, Hanau (DE)

(72) Inventors: Ulrich Hausch, Frankfurt (DE); Michael Schäfer, Künzell (DE); Jens Nachreiner, Schlüchtern (DE)

(73) Assignee: Heraeus Deutschland GmbH & Co. KG, Hanau (DE)

( * ) Notice: Subject to any disclaimer, the term of this patent is extended or adjusted under 35 U.S.C. 154(b) by 481 days.

(21) Appl. No.: 15/680,124

(22) Filed: Aug. 17, 2017

(65) Prior Publication Data
US 2018/0050211 A1    Feb. 22, 2018

(30) Foreign Application Priority Data
Aug. 17, 2016 (EP) ..................................... 16184554

(51) Int. Cl.
| | | |
|---|---|---|
| *A61N 1/375* | (2006.01) | |
| *A61B 5/318* | (2021.01) | |
| *H02G 15/013* | (2006.01) | |

(52) U.S. Cl.
CPC ............ *A61N 1/3754* (2013.01); *A61B 5/318* (2021.01); *A61N 1/37512* (2017.08); *H02G 15/013* (2013.01)

(58) Field of Classification Search
CPC .............................. A61N 1/375; A61N 1/3754
See application file for complete search history.

(56) References Cited

U.S. PATENT DOCUMENTS

| | | | |
|---|---|---|---|
| 2004/0257747 A1* | 12/2004 | Stevenson | ............ A61N 1/3754 361/302 |
| 2005/0197677 A1* | 9/2005 | Stevenson | ................ A61N 1/37 607/36 |
| 2007/0083244 A1* | 4/2007 | Stevenson | .............. A61N 1/375 607/37 |
| 2012/0164550 A1* | 6/2012 | Ohmori | ............... H01M 8/2485 429/456 |
| 2012/0193125 A1* | 8/2012 | Pavlovic | ............. A61N 1/3754 174/152 GM |
| 2012/0193141 A1 | 8/2012 | Reisinger et al. | |
| 2012/0194981 A1 | 8/2012 | Kempf et al. | |
| 2013/0092956 A1* | 4/2013 | Ishibashi | ........... H01L 29/66068 257/77 |
| 2013/0338750 A1 | 12/2013 | Eck et al. | |
| 2014/0134513 A1* | 5/2014 | Nakamura | .......... H01M 8/0258 429/452 |
| 2015/0122875 A1 | 5/2015 | Pavlovic et al. | |
| 2017/0140847 A1* | 5/2017 | Kamikoriyama | ........ H01B 1/22 |

FOREIGN PATENT DOCUMENTS

EP           1897589           3/2008

* cited by examiner

*Primary Examiner* — George R Evanisko
(74) *Attorney, Agent, or Firm* — Dicke, Billig & Czaja, PLLC

(57) ABSTRACT

One aspect relates to an apparatus including a first frame, a further frame, a first element, a second element, and a third element. The first frame frames the further frame, the further frame frames the first element, and electrically insulates the first element and the first frame from each other. The first element is electrically conductive, the second element is electrically conductive, and the third element provides an electrically conductive connection between the first element and the second element, and has a porosity in the range of 0.001 to 0.4.

9 Claims, 9 Drawing Sheets

100

100

100

500

600

700

800

900

ELECTRICAL FEEDTHROUGH WITH A SINTERED ELECTRICAL CONNECTION

CROSS-REFERENCE TO RELATED APPLICATIONS

This Utility Patent Application claims priority to European Patent Application No. EP 16184554.0, filed on Aug. 17, 2016, which is incorporated herein by reference.

BACKGROUND

One aspect relates to an apparatus comprising a first frame, a further frame, a first element, a second element and a third element, wherein the third element provides an electrically conductive connection between the first element and the second element and has a porosity in the range of 0.001 to 0.4; an apparatus precursor comprising a first frame, a further frame and a first element, wherein a contact surface of the first element has a composition at least partially superimposed onto it; a method comprising provision of a feedthrough, obtaining of an element precursor and heating of the element precursor; an apparatus obtainable by the above-mentioned method; an implantable electrical medical device; a method for producing an implantable electrical medical device; an implantable electrical medical device obtainable by the above method; and a use of a composition for an electrically conductive connection of a feedthrough element and an electrical conductor.

Electrical feedthroughs are commonly used in the prior art in order to establish an electrical connection between an interior space of a hermetically sealed housing of an electrical device and an exterior space of this housing. For example, electrical devices with a hermetically sealed housing are electrical medical implantable devices. These can be active, electrical impulse-emitting devices such as pacemakers, defibrillators or cochlear implants; but also passive electrical signal-measuring devices such as EKG devices. Examples of pacemakers known in prior art are bladder pacemakers, diaphragmatic pacemakers, intestinal pacemakers, respiratory pacemakers, brain pacemakers and cardiac pacemakers. In the above-mentioned implantable medical devices, the hermetically sealed housing is typically a metal housing having a header or header block on a side facing the interior or the exterior, that is, a connecting piece with connection sockets for the connection of electrical lines. In a cardiac pacemaker, the connection sockets have electrical contacts via which the electrode lines in the external space can be electrically connected to control electronics in the internal space of the hermetically sealed housing. For implantable devices, this hermetic sealing is of vital importance. Therefore, each electrical feedthrough must also be hermetically sealed. Such a feedthrough ordinarily contains an electrical line connecting the internal space and the external space, which is formed by an electrically conductive connecting pin, that extends into an electrically insulating insulator body via a through opening. The electrically conductive connecting pin protrudes on both sides beyond the respective front surface of the insulator body, so that respective continuing electrical lines can be connected to the connecting pin on both sides of the insulator body and thus both sides of the electrical feedthrough. It is proposed in the prior art, such as in EP 1897589 A2, that this connection be carried out by soldering or welding.

The electrical feedthroughs of the prior art have at least the following drawbacks. The electrical conductivity of an electrical connection soldered or welded to a connecting pin is limited, for example by the selection of suitable solders or by the minimum thickness of the soldered or welded connection. Moreover, soldered or welded electrical connections commonly have a meniscus, which can result in an electrical malfunction, specifically a short circuit, of the feedthrough. Accordingly, such a meniscus limits the miniaturization of electrical feedthroughs. A soldered or welded electrical connection to a feedthrough must be cleaned after the soldering or welding. This gives rise to the risk that contaminants may be introduced. In order to connect electrical lines to feedthroughs of the prior art, metal alloys or metal mixtures must be used. This can lead to the formation of intermetallic phases and thus to tears or to reduced durability of the connection and thus the feedthrough. All of the above-mentioned risks, defects, or limitations on durability illustrated by the electrical feedthroughs of the prior art are of particular importance in implantable medical devices, as in this case, the patient's well-being is directly affected by malfunctions or the need to replace a defective device. Moreover, in the prior art, electrically connecting a cermet connecting pin of a feedthrough is impossible or only possible at considerable expense. In soldering of porous materials such as cermet, there is a risk that the solder used will be absorbed by the pores of the material.

For these and other reasons, a need exists for the present embodiments.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 1b is a schematic sectional view of the apparatus according to the embodiment in FIG. 1a.

DETAILED DESCRIPTION

Figure 1A:
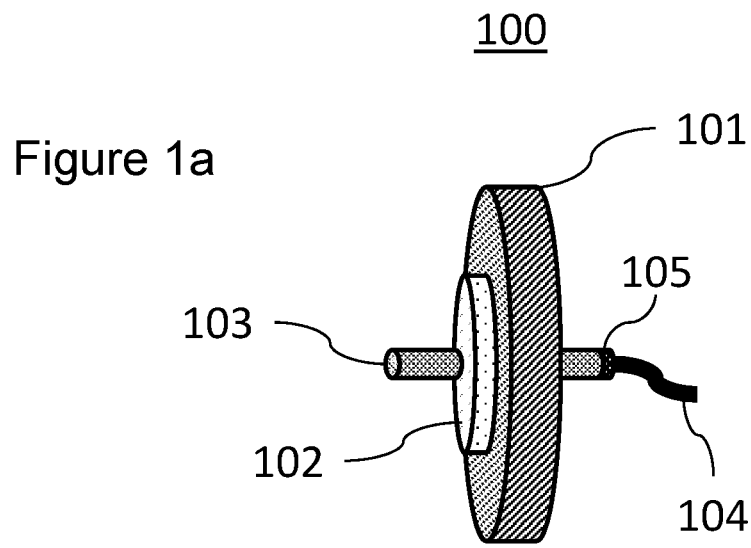
FIG. 1a is a schematic view of an apparatus according to one embodiment.

In the following Detailed Description, reference is made to the accompanying drawings, which form a part hereof, and in which is shown by way of illustration specific embodiments in which the embodiments may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present embodiments. The following detailed description, therefore, is not to be taken in a limiting sense, and the scope of the present embodiments are defined by the appended claims.

It is to be understood that the features of the various exemplary embodiments described herein may be combined with each other, unless specifically noted otherwise.

One embodiment at least partly overcomes a drawback of the prior art. One embodiment provides an implantable electrical medical device with an improved electrical connection between a cermet feedthrough and an electrical line. One embodiment provides a feedthrough for an implantable electrical medical device that has low electrical resistance. One embodiment provides an implantable electrical medical device with an electrical connection to an electrical feedthrough, wherein the electrical connection contains no meniscus. One embodiment provides an implantable electrical medical device with a low risk of causing a defect such as a short circuit. One embodiment provides an implantable electrical medical device with a low pitch of a feedthrough. One embodiment provides an implantable electrical medical device with a feedthrough, wherein the distance between a connecting pin of the feedthrough and an electrical line connected thereto is shorter. One embodiment provides a miniaturized electrical feedthrough for an implantable electrical medical device. One embodiment provides an implantable electrical medical device with an electrical connection to an electrical feedthrough, wherein the electrical connection is composed of a pure metal or contains no metal alloy or both. One embodiment provides an implantable electrical medical device with an electrical connection to an electrical feedthrough, wherein the electrical connection is characterized by higher durability, or a lower risk of material defects such as tears, or both. One embodiment provides an implantable electrical medical device that can be produced in a less complex manner or less expensively or both. One embodiment provides a method for producing an implantable electrical medical device that is less complex or less expensive or both. One embodiment provides an implantable electrical medical device with increased efficiency. One embodiment provides an implantable electrical medical device with lower energy consumption. One embodiment provides an implantable electrical medical device with a longer battery life. One embodiment provides an implantable electrical medical device with increased operational safety. One embodiment provides an implantable electrical medical device with a reduced number of connection sites. One embodiment provides an implantable electrical medical device with an increased functional life. One embodiment provides an implantable electrical medical device that is less prone to malfunctions. One embodiment provides a method for producing one of the above advantageous implantable electrical medical devices. One embodiment provides an improved implantable electrical medical device. One embodiment provides an improved treatment for bradycardia or tachycardia or both. One embodiment provides a more economical treatment for bradycardia or tachycardia or both. One embodiment provides a gentler treatment for bradycardia or tachycardia or both. One embodiment provides a treatment for bradycardia or tachycardia or both that involves fewer surgical interventions. One embodiment provides a lower-risk treatment for bradycardia or tachycardia or both. One embodiment provides a method for electrically connecting a feedthrough of an implantable electrical medical device to an electrical line, wherein the method involves a lower risk of the introduction of contaminants. One embodiment provides a method for improved electrical connection of a cermet feedthrough of an implantable electrical medical device to an electrical line. One embodiment provides a cardiac pacemaker or an implantable EKG device or both, which has/have one of the advantages or a balanced combination of two or more of the advantages of the above-mentioned implantable electrical medical devices.

An embodiment 1 of an apparatus 1 comprising a first frame, a further frame, a first element, a second element and a third element contributes towards meeting at least one of the above according to one embodiment;
wherein
a) the first frame frames the further frame;
b) the further frame
  i) frames the first element, and
  ii) electrically insulates the first element and the first frame from each other;
c) the first element is electrically conductive;
d) the second element is electrically conductive; and
e) the third element
  i) provides an electrically conductive connection between the first element and the second element, and
  ii) has a porosity in the range of 0.001 to 0.4, in one embodiment 0.01 to 0.3, in one embodiment 0.05 to 0.25, in one embodiment 0.1 to 0.2, and in one embodiment 0.13 to 0.16.

An inventive embodiment 2 of the apparatus 1 is configured according to embodiment 1, wherein the first element includes a cermet and is in one embodiment composed thereof.

An inventive embodiment 3 of the apparatus 1 is configured according to embodiment 1 or 2, wherein the further frame includes a ceramic and is in one embodiment composed thereof.

An inventive embodiment 4 of the apparatus 1 is configured according to one of the above embodiments, wherein the further frame and the first element are configured in one piece. In one embodiment, the further frame and the first element are composed of different materials that are directly bonded to each other. In one embodiment, a directly bonded connection contains no soldered connections or no welded joints or both. In one embodiment, the further frame and the first element are produced in a production method as a single piece without assembling prefabricated parts.

An inventive embodiment 5 of the apparatus 1 is configured according to one of the above embodiments, wherein the second element is selected from the group composed of an electrical contact, a conductive path, a wire, a socket, and a plug, or a combination of at least two of these components.

An inventive embodiment 6 of the apparatus 1 is configured according to one of the above embodiments, wherein the first element or the second element or both is/are connected to an electrotechnical filter. In one embodiment, the first element or the second element or both is/are connected to the electrotechnical filter in a mechanical or electrically conductive manner or both. In one embodiment, an electrotechnical filter is an MLCC filter. In one embodiment, the electrotechnical filter is arranged on one side of the first frame that faces towards the second element.

An inventive embodiment 7 of the apparatus 1 is configured according to one of the above embodiments, wherein the third element meets one or at least 2, in one embodiment at least 3, in one embodiment at least 4, in one embodiment at least 5, in one embodiment at least 6, and in one embodiment at least 7 of the following criteria:
- a) it has an electrical resistance of a maximum of 0.02 mΩ·cm, in one embodiment a maximum of 0.015 mΩ·cm, and in one embodiment a maximum of 0.01 mΩ·cm;
- b) it has a layer thickness in the range of 0.005 to 1 mm, in one embodiment 0.01 to 1 mm, in one embodiment 0.05 to 1 mm, in one embodiment 0.1 to 0.8 mm, and in one embodiment 0.2 to 0.6 mm;
- c) it is composed of a metal or a metal mixture or both, wherein the third element has a bulk density in the range of 60 to 99.9%, in one embodiment 70 to 99%, in one embodiment 75 to 95%, in one embodiment 80 to 90%, and in one embodiment 84 to 87%, based on the true density of the metal or the metal mixture;
- d) it includes only one metal in an amount of more than 0.05 wt. %, in one embodiment more than 0.03 wt. %, in one embodiment more than 0.01 wt. %, based in each case on the weight of the third element;
- e) it includes no meniscus;
- f) it includes an element selected from the group composed of Ag, Au, Cu, Pt and Pd, or a combination of at least two of these in an amount in the range of 10 to 100 wt. %, in one embodiment 20 to 100 wt. %, in one embodiment 30 to 100 wt. %, in one embodiment 40 to 100 wt. %, in one embodiment 50 to 100 wt. %, in one embodiment 60 to 100 wt. %, in one embodiment 70 to 100 wt. %, in one embodiment 80 to 100 wt. %, in one embodiment 90 to 100 wt. %, in one embodiment 95 to 100 wt. %, in one embodiment 98 to 100 wt. %, and in one embodiment 99 to 100 wt. % based on the weight of the third element;
- g) at least 50%, in one embodiment at least 60%, in one embodiment at least 70%, in one embodiment at least 80%, in one embodiment at least 90%, in one embodiment at least 95%, and in one embodiment 100% of the grains of the third element have a grain size in the range of 1 to 500 nm, in one embodiment 5 to 450 nm, in one embodiment 10 to 400 nm, in one embodiment 50 to 350 nm, in one embodiment 100 to 300 nm, and in one embodiment 150 to 250 nm;
- h) at least 50%, in one embodiment at least 60%, in one embodiment at least 70%, in one embodiment at least 80%, in one embodiment at least 90%, in one embodiment at least 95%, and in one embodiment 100%, of the pores of the third element have a pore size in the range of 0.5 to 1.5 μm, in one embodiment 0.6 to 0.9 μm, and in one embodiment 0.6 to 0.8 μm.

In one embodiment, the third element meets each of the above criteria. Under item f), in one embodiment Ag or Au or both are particularly preferred. If the apparatus according to the embodiment is an electrical feedthrough in a housing,
- a) the third element in one embodiment includes Ag if the second element is inside the housing; and
- b) the third element in one embodiment includes Au if the second element is outside the housing.

An inventive embodiment 8 of the apparatus 1 is configured according to one of the above embodiments, wherein the electrically conductive connection has an electrical resistance in the range of 0.001 to 10 mΩ, in one embodiment 0.01 to 9 mΩ, in one embodiment 0.05 to 8 mΩ, in one embodiment 0.075 to 7.5 mΩ, in one embodiment 0.1 to 6 mΩ, and in one embodiment 0.5 to 5 mΩ.

An embodiment 1 of an apparatus precursor 1 comprising a first frame, a further frame and a first element contributes towards meeting at least one of the above according to the embodiment;
wherein
- a) the first frame frames the further frame;
- b) the further frame
  - i) frames the first element, and
  - ii) electrically insulates the first element and the first frame from each other; and
- c) the first element
  - i) is electrically conductive, and
  - ii) includes a first contact surface;

wherein a composition comprising a liquid and a plurality of metal particles is at least partially superimposed onto the first contact surface. In one embodiment, a first frame is a first frame according to the apparatus 1. In one embodiment, a further frame is a further frame according to the apparatus 1 of the embodiment. In one embodiment, a first element is a first element according to the apparatus 1 of the embodiment.

An inventive embodiment 2 of the apparatus precursor 1 is configured according to embodiment 1, wherein the composition meets 1 or at least 2, in one embodiment at least 3, in one embodiment at least 4, in one embodiment at least 5, in one embodiment at least 6, and in one embodiment at least 7 of the following criteria:
- a) it includes the plurality of metal particles in an amount in the range of 75 to 99 wt. %, in one embodiment 80 to 98 wt. %, in one embodiment 85 to 95 wt. %, and in one embodiment 88 to 93 wt. %, based in each case on the weight of the composition;
- b) it includes the liquid in an amount in the range of 1 to 25 wt. %, in one embodiment 2 to 20 wt. %, in one embodiment 5 to 15 wt. %, and in one embodiment 7 to 12 wt. %, based in each case on the weight of the composition;
- c) it includes only one metal in an amount of more than 0.05 wt. %, in one embodiment more than 0.03 wt. %, in one embodiment more than 0.01 wt. %, based in each case on the weight of the composition;
- d) it has a viscosity in the range of 50 to 500 Pa·s, in one embodiment 75 to 450 Pa·s, in one embodiment 100 to 400 Pa·s, and in one embodiment 150 to 350 Pa·s;
- e) at least a portion of the plurality of metal particles includes one selected from the group composed of Ag, Au, Cu, Pt, and Pd, or a combination of at least two of these in an amount in the range of 10 to 100 wt. %, in one embodiment 20 to 100 wt. %, in one embodiment 30 to 100 wt. %, in one embodiment 40 to 100 wt. %, in one embodiment 50 to 100 wt. %, in one embodiment 60 to 100 wt. %, in one embodiment 70 to 100 wt. %, in one embodiment 80 to 100 wt. %, in one embodiment 90 to 100 wt. %, in one embodiment 95 to 100 wt. %, in one embodiment 98 to 100 wt. %, and in one embodiment 99 to 100 wt. %, based on the total weight of the portion of the plurality of metal particles;
- f) the metal particles have a particle size distribution characterized by a $D_{50}$ in the range of 0.1 to 20 μm, in one embodiment 1 to 15 μm, and in one embodiment 2 to 10 μm;
- g) the metal particles have a mass-specific surface area in the range of 0.5 to 5 $m^2$/kg, in one embodiment 1 to 4 $m^2$/kg, and in one embodiment 2 to 3 $m^2$/kg;

h) it includes no halogen in an amount of more than 1500 ppm, in one embodiment more than 1000 ppm, and in one embodiment more than 500 ppm, based in each case on the weight of the composition.

In one embodiment, the composition meets each of the above criteria.

An embodiment 1 of a method 1 comprising the following method steps contributes towards meeting at least one of the above according to the embodiment:
- a) provision of a feedthrough comprising a first frame, a further frame, and a first element,
  wherein
  - i) the first frame frames the further frame,
  - ii) the further frame
    - A. frames the first element, and
    - B. electrically insulates the first frame and the first element from each other, and
  - iii) the first element
    - A. is electrically conductive, and
    - B. includes a first contact surface;
- b) provision of a second element comprising a further contact surface;
- c) provision of a composition comprising a liquid and a plurality of metal particles,
  wherein the metal particles include a metal having a lowest melting temperature;
- d) superimposing the composition onto the first contact surface or the further contact surface or both;
- e) connecting the first contact surface and the further contact surface via the composition;
- f) reducing the amount of liquid in the composition, in one embodiment by at least 80 wt. %, in one embodiment at least 85 wt. %, in one embodiment at least 90 wt. %, and in one embodiment at least 95 wt. %, based on the amount of liquid in the composition immediately prior to method step f), thereby obtaining an element precursor; and
- g) heating of the element precursor to a temperature in the range of 10 to 90%, in one embodiment 10 to 80%, in one embodiment 10 to 70%, in one embodiment 10 to 60%, in one embodiment 15 to 50%, in one embodiment 15 to 40%, and in one embodiment 15 to 35%, of the lowest melting temperature thereby obtaining a third element.

One reduction method in method step f) is an expulsion. One expulsion method is a debinding. One debinding method is one selected from the group composed of thermal, catalytic, and solvent debinding, or a combination of at least two of these. One element precursor is a green part or a brown part or both. One first frame is a first frame according to the apparatus 1 of the embodiment. One further frame is a further frame according to the apparatus 1 of the embodiment. One first element is a first element according to the apparatus 1 of the embodiment. One second element is a second element according to the apparatus 1 of the embodiment. One third element is a third element according to the apparatus 1 of the embodiment. One composition is the composition according to the apparatus precursor 1 of the embodiment. In one embodiment, an apparatus precursor 1 of the embodiment is obtained in method step d). In one embodiment, the heating in method step g) is carried out to a maximum temperature in the range of 150 to 350° C., in one embodiment 180 to 320° C., in one embodiment 200 to 300° C., and in one embodiment 220 to 290° C. The above-mentioned maximum temperature is in one embodiment maintained for 0.5 to 20 minutes in one embodiment 0.5 to 7 minutes, and in one embodiment 0.5 to 5 minutes. In one embodiment, method step g) is carried out in a sintering press.

An inventive embodiment 2 of the method 1 is configured according to embodiment 1, wherein the reduction in method step f) includes heating of the composition to a temperature in the range of 50 to 160° C., in one embodiment 70 to 150° C., in one embodiment 80 to 130° C., and in one embodiment 90 to 110° C. The above-mentioned temperature is in one embodiment a maximum temperature in method step f). The above-mentioned temperature is in one embodiment maintained for 0.5 to 30 minutes, in one embodiment 1 to 25 minutes, and in one embodiment 3 to 20 minutes. In method step f), the element precursor is in one embodiment in air. Also in one embodiment, method step f) is carried out in a chamber furnace or a chamber dryer or both.

An inventive embodiment 3 of the method 1 is configured according to embodiment 1 or 2, wherein method step g) meets 1 or at least 2, in one embodiment at least 3 of the following criteria:
- a) the element precursor is subjected in method step g) to a mechanical pressure in the range of 0 to 50 MPa, in one embodiment 5 to 45 MPa, in one embodiment 10 to 40 MPa, and in one embodiment 15 to 35 MPa;
- b) while the third element is being obtained, the element precursor or the third element or both are under an inert gas atmosphere;
- c) a distance of the first contact surface from the further contact surface is reduced in method step g) by 0.01 to 5%, in one embodiment 0.05 to 4.5%, in one embodiment 0.1 to 4%, in one embodiment 0.5 to 3.5%, and in one embodiment 1 to 3%, based on the distance immediately prior to method step g), to a value in the range of 0.005 to 1 mm, in one embodiment 0.01 to 1 mm, in one embodiment 0.05 to 1 mm, in one embodiment 0.1 to 0.8 mm, and in one embodiment 0.2 to 0.6 mm;
- d) the temperature mentioned in method step g) is maintained for a duration in the range of 0.5 to 120 min, in one embodiment 0.7 to 50 min, in one embodiment 1 to 20 min, in one embodiment 1 to 10 min, in one embodiment 1 to 5 min.

In one embodiment, the method step g) fulfills one of the following combinations of the above criteria: a) b) c) d), and a) c) d).

In one embodiment, a mechanical pressure is exerted on the element precursor by a solid, in one embodiment a pressure casting die. In one embodiment, an inert gas atmosphere includes one gas from the group composed of:
- oxygen in an amount of less than 20 wt. %, in one embodiment less than 15 wt. %, in one embodiment less than 10 wt. %, and in one embodiment less than 5 wt. %, based on the inert gas atmosphere;
- $H_2O$ in an amount of less than 5 wt. %, in one embodiment less than 4 wt. %, in one embodiment less than 3 wt. %, and in one embodiment less than 2 wt. %, based on the inert gas atmosphere;
- CO in an amount of less than 1 wt. %, in one embodiment less than 0.8 wt. %, and in one embodiment less than 0.5 wt. %, based on the inert gas atmosphere; and $CO_2$ in an amount of less than 4 wt. %, in one embodiment less than 3 wt. %, in one embodiment less than 2 wt. %, and in one embodiment less than 1 wt. %, based on the inert gas atmosphere; or
- a combination of at least two of these gases.

In one embodiment, an inert gas atmosphere is characterized by a gas pressure in the range of 0.1 to 1100 mbar, in one embodiment 0.5 to 1000 mbar, in one embodiment 1 to 900 mbar, in one embodiment 10 to 800 mbar, in one embodiment 50 to 700 mbar in one embodiment 100 to 600 mbar, and in one embodiment 200 to 500 mbar. In a further embodiment, the element precursor in method step g) is in air.

An inventive embodiment 4 of the method 1 is configured according to one of the embodiments 1 to 3, wherein the superimposing method is one selected from the group composed of dispensing, dipping, printing, spreading, and blade coating, or a combination of at least two of these methods. In one embodiment, a printing method is screen printing. In screen printing, the composition is pressed e through at least one opening, in one embodiment through a plurality of openings, in a screen.

An inventive embodiment 5 of the method 1 is configured according to one of the embodiments 1 to 4, wherein according to method step g), the third element is not cleaned. In this case, cleaning is treatment of the third element in order to reduce or eliminate contamination of the third element. In one embodiment, according to method step g), the third element is not brought into contact with a cleaning agent or a cleaning tool or both. In one embodiment, a cleaning agent is a solution comprising a solvent, or a fluxing agent, or both in an amount of at least 40 wt. %, in one embodiment at least 50 wt. %, in one embodiment at least 60 wt. %, in one embodiment at least 70 wt. %, in one embodiment at least 80 wt. %, and in one embodiment at least 90 wt. %. In one embodiment, a solvent is an alcohol or acetone or both. In one embodiment, an alcohol is isopropanol. In one embodiment, a cleaning tool is a glass etcher.

An inventive embodiment 6 of the method 1 is configured according to one of the embodiments 1 to 5, wherein the composition meets 1 or at least 2, in one embodiment at least 3, in one embodiment at least 4, in one embodiment at least 5, in one embodiment at least 6, and in one embodiment at least 7 of the following criteria:
a) it includes the plurality of metal particles in an amount in the range of 75 to 99 wt. %, in one embodiment 80 to 98 wt. %, in one embodiment 85 to 95 wt. %, and in one embodiment 88 to 93 wt. % based on the weight of the composition;
b) it includes the liquid in an amount in the range of 1 to 25 wt. %, in one embodiment 2 to 20 wt. %, in one embodiment 5 to 15 wt. %, and in one embodiment 7 to 12 wt. %, based in each case on the weight of the composition;
c) it includes only one metal in an amount of more than 0.05 wt. %, in one embodiment more than 0.03 wt. %, in one embodiment more than 0.01 wt. %, based in each case on the weight of the composition;
d) it has a viscosity in the range of 50 to 500 Pa·s, in one embodiment 75 to 450 Pa·s, in one embodiment 100 to 400 Pa·s, and in one embodiment 150 to 350 Pa·s;
e) at least a portion of the plurality of metal particles includes one selected from the group composed of Ag, Au, Cu, Pt, and Pd, or a combination of at least two of these in an amount in the range of 10 to 100 wt. %, in one embodiment 20 to 100 wt. %, in one embodiment 30 to 100 wt. %, in one embodiment 40 to 100 wt. %, in one embodiment 50 to 100 wt. %, in one embodiment 60 to 100 wt. %, in one embodiment 70 to 100 wt. %, in one embodiment 80 to 100 wt. %, in one embodiment 90 to 100 wt. %, in one embodiment 95 to 100 wt. %, in one embodiment 98 to 100 wt. %, and in one embodiment 99 to 100 wt. %, based on the total weight of the portion of the plurality of metal particles;
f) the metal particles have a particle size distribution characterized by a $D_{50}$ in the range of 0.1 to 20 µm, in one embodiment 1 to 15 µm, and in one embodiment 2 to 10 µm;
g) the metal particles have a mass-specific surface area in the range of 0.5 to 5 $m^2$/kg, in one embodiment 1 to 4 $m^2$/kg, and in one embodiment 2 to 3 $m^2$/kg;
h) it includes no halogen in an amount of more than 1500 ppm, in one embodiment more than 1000 ppm, and in one embodiment more than 500 ppm, based in each case on the weight of the composition.

In one embodiment, the composition meets each of the above criteria.

An embodiment 1 of an apparatus 2, obtainable by the method 1 according to one of its embodiments 1 to 5, contributes towards meeting at least one of the above according to the embodiment. In one embodiment, components and elements of the apparatus 2 are configured according to one of the embodiments of the apparatus 1.

An embodiment 1 of an implantable electrical medical device 1 comprising a housing and an apparatus 1 according to one of its embodiments 1 to 8, or an apparatus 2 according to its embodiment 1, contributes towards meeting at least one of the above according to the embodiment; wherein the housing includes a housing opening; wherein the housing opening includes the first frame. In one embodiment, the housing is hermetically sealed. In one embodiment, the apparatus 1 or the apparatus 2 seals the housing opening hermetically.

An embodiment 1 of a method 2 for producing an implantable electrical medical device comprising a housing comprising a housing opening contributes towards meeting at least one of the above according to the embodiment, wherein in a method step, an apparatus 1 according to one of its embodiments 1 to 8, or an apparatus 2 according to its embodiment 1, or an apparatus precursor 1 according to one of its embodiments 1 or 2 is inserted into the housing opening such that the housing opening includes the first frame. In one embodiment, the apparatus 1, or the apparatus 2, or the apparatus precursor 1 is inserted into the housing opening such that the housing opening is closed in a hermetically sealed manner. For this purpose, the apparatus 1, or the apparatus 2, or the apparatus precursor 1 can be soldered or welded or both into the housing opening. In one embodiment, the first frame is composed of the same material as the housing and is welded into the housing opening.

An embodiment 1 of an implantable electrical medical device 2, obtainable by the method 2 according to its embodiment 1, contributes towards meeting at least one of the above according to the embodiment.

An embodiment 1 of a use 1 of a composition comprising a liquid and a plurality of metal particles for an electrically conductive connection of a feedthrough element and an electrical conductor contributes towards meeting at least one of the above according to the embodiment; wherein the use includes sintering of the composition. In one embodiment, a composition is the composition according to the apparatus precursor 1 of the embodiment or the method 1 according to the embodiment or both.

An embodiment 1 of a method 3 comprising the following as method steps contributes towards meeting at least one of the above according to the embodiment:

a) provision of an implantable electrical medical device 1 according to its embodiment 1 or an implantable electrical medical device 2 according to its embodiment 1; and b) insertion of the implantable electrical medical device into an eukaryotic organism.

In one embodiment, an insertion method is implantation. In one embodiment, a eukaryotic organism is a human or an animal or both. In one embodiment, an insertion is carried out into a body part selected from the group composed of the chest, the heart, the thorax, the stomach cavity, the abdomen, the head, the skull, or the inner ear, or a combination of at least two of these body parts.

An embodiment 1 of a use 2 of an implantable electrical medical device 1 according to its embodiment 1 or of an implantable electrical medical device 2 according to its embodiment 1 in a treatment of a disease or a dysfunction or both contributes towards meeting at least one of the above according to the embodiment.

Frame

According to one embodiment, a frame is a torus, toroidal, or a prism, wherein the prism includes a first bottom surface and a second bottom surface and at least one cavity, wherein the cavity includes a partial surface of the first bottom surface and a partial surface of the second bottom surface. The cavity is a frame opening. In one embodiment, a first bottom surface or a second bottom surface or both are selected from the group composed of a circular surface, an elliptical surface, an oval surface, a triangular surface, a square surface, a pentagonal surface, a hexagonal surface, a heptagonal surface, an octagonal surface, a polygonal surface or a combination of at least two such surfaces. The partial surface of the first bottom surface or the partial surface or second bottom surface or both contained in the frame opening are in one embodiment selected from the group composed of a circular surface, an elliptical surface, an oval surface, a triangular surface, a square surface, a pentagonal surface, a hexagonal surface, a heptagonal surface, an octagonal surface, a polygonal surface or a combination of at least two such surfaces. In one embodiment, a polygonal surface is a surface of a regular polygon or a surface of an irregular polygon. In one embodiment, a frame is a hollow cylinder or a ring or both. In one embodiment, a frame is a perforated plate. A perforated plate is a plate comprising a plurality of holes connecting surfaces opposite one another. In one embodiment, a first frame according to the embodiment is a flange. In one embodiment, a first frame is composed of a metal. In one embodiment, a frame according to the embodiment is a feedthrough sleeve. In one embodiment, a further frame is composed of a ceramic.

First Element

In one embodiment, a first element according to the embodiment is a feedthrough element or a connecting pin, also referred to as a connection pin, or both. In one embodiment, a first element is composed of a cermet.

Metal for the Housing or First Frame

For the metal composing the housing or the first frame or both, in one embodiment both, all metals known to the person skilled in the art that illustrate conductivity as well as favourable compatibility with eukaryotic tissue can be used. A metal according to one embodiment is selected from the group composed of platinum, iridium, niobium, palladium, iron, stainless steel, cobalt-chromium alloy, molybdenum, tantalum, tungsten, titanium, cobalt and zirconium or a combination of at least two thereof. In one embodiment, a combination is an alloy. In one embodiment, a stainless steel is stainless steel 316L. In one embodiment, a metal is biocompatible. In one embodiment, an alloy is biocompatible.

Biocompatible Material

In one embodiment, a biocompatible material is selected from the group composed of biotolerant, bioinert and bioactive materials or a combination of at least two such materials.

Eukaryotic Tissue

In one embodiment, a eukaryotic tissue is an animal tissue or a human tissue or both.

Cermet

According to one embodiment, "cermet" refers to a composite material of one or a plurality of ceramic materials in at least one metallic matrix or a composite material of one or a plurality of metallic materials in at least one ceramic matrix or both. For example, a mixture of at least one ceramic powder and at least one metallic powder, which can be supplemented for example by at least one binder and optionally by at least one solvent, can be used to produce a cermet. The ceramic powder(s) of the cermet in one embodiment have a mean particle size of less than 10 µm, in one embodiment less than 5 µm, and in one embodiment less than 3 µm. The metallic powder(s) of the cermet in one embodiment have a mean particle size of less than 15 µm, in one embodiment less than 10 µm, and in one embodiment less than 5 µm. Mean particle size is considered for example, to refer to the median value or $D_{50}$ value of the particle size distribution. The $D_{50}$ value describes the value at which 50% of the particles of the ceramic powder and/or the metallic powder are finer than the $D_{50}$ value. In one embodiment, a cermet has a high specific conductivity that is in one embodiment at least 1 S/m, in one embodiment at least 100 S/m, in one embodiment at least $10^3$ S/m, in one embodiment at least $10^4$ S/m, even in one embodiment at least $10^5$ S/m, and in one embodiment at least $10^6$ S/m.

The at least one ceramic component of a cermet according to one embodiment includes a ceramic according to the embodiment. The at least one metallic component of a cermet according to one embodiment includes a one selected from the group composed of platinum, iridium, niobium, palladium, iron, stainless steel, a cobalt-chromium alloy, molybdenum, tantalum, tungsten, titanium, cobalt and zirconium or a combination of at least two thereof. In this case, a combination is an alloy. In one embodiment, a stainless steel is the stainless steel 316L. In the case of cermet, as a rule, an electrically conductive connection is established when the metal content is above the so-called percolation threshold, at which the metal particles in the sintered cermet are connected to one another at least at individual locations, such that electrical conduction is possible. Experience has illustrated that for this purpose, depending on the material selected, the metal content should be at least 25 vol. %, in one embodiment at least 32 vol. %, and in one embodiment at least 38 vol. %, based in each case on the total volume of the cermet.

Ceramics

A ceramic according to one embodiment can be any ceramic that the person skilled in the art would select for the use according to the embodiment. The ceramic is in one embodiment selected from the group composed of an oxide ceramic, a silicate ceramic, a non-oxide ceramic or a mixture of at least two of these.

The oxide ceramic is in one embodiment selected from the group composed of a metal oxide, a metalloid oxide or a mixture thereof. The metal of the metal oxide can be selected from the group composed of aluminium, beryllium, barium, calcium, magnesium, sodium, potassium, iron, zirconium, titanium or a mixture of at least two of these metals. The metal oxide is in one embodiment selected from the group composed of aluminium oxide ($Al_2O_3$), magnesium oxide (MgO), zirconium oxide ($ZrO_2$), yttrium oxide ($Y_2O_3$), aluminium titanate ($Al_2TiO_5$), a piezoceramic such as lead zirconate ($PbZrO_3$), lead titanate ($PbTiO_3$) and lead zirconate titanate (PZT) or a mixture of at least two thereof. The metalloid of the metalloid oxide is in one embodiment selected from the group composed of boron, silicon, arsenic, tellurium or a mixture of at least two thereof. In one embodiment, a oxide ceramic includes an oxide selected from the group composed of zirconium oxide toughened aluminium oxide (ZTA—$Al_2O_3/ZrO_2$), yttrium toughened zirconium oxide (Y-TZP), barium (Zr, Ti)oxide, barium (Ce, Ti)oxide or a combination of at least two of these oxides.

The silicate ceramic is in one embodiment selected from the group composed of steatite ($Mg_3[Si_4O_{10}(OH)_2]$), cordierite ($(Mg, Fe^{2+})_2(Al_2Si)[Al_2Si_4O_{18}]$), mullite ($Al_2Al_{2+2x}Si_{2-2x}O_{10-x}$, where x=number of oxygen vacancies per unit cell), feldspar (Ba, Ca, Na, K, $NH_4$)(Al, B, Si)$_4O_8$) or a mixture of at least two of these.

The non-oxide ceramic can be selected from the group composed of a carbide, a nitride or a mixture thereof. The carbide can be selected from the group composed of silicon carbide (SiC), boron carbide ($B_4C$), titanium carbide (TiC), tungsten carbide, cementite ($Fe_3C$). The nitride can be selected from the group composed of silicon nitride ($Si_3N_4$), aluminium nitride (AlN), titanium nitride (TiN), silicon aluminium oxynitride (SIALON) or a mixture of at least two of these. In one embodiment, a non-oxide ceramic is sodium potassium niobate.

Hermetically Sealed

Within the framework of one embodiment, the term "hermetically sealed" can illustrate that in use as intended within the usual periods of time (for example 5 to 10 years), moisture or gases or both cannot or can only minimally be exchanged through a hermetically sealed barrier. A physical parameter that can for example describe a permeation of gases or moisture or both through the barrier is the so-called leak rate, which can be determined for example by means of leak tests. Corresponding leak tests can be carried out, for example, with helium leak testers and/or mass spectrometers and are specified in the standard Mil-STD-883G Method 1014. In this case, the maximum allowable helium leak rate is determined independently of the internal volume of the apparatus to be tested. According to the methods specified in MIL-STD-883G, Method 1014, Paragraph 3.1, and taking into account the volumes and cavities of the apparatuses to be tested in use of the present embodiment, these maximum allowable helium leak rates can for example be $1\times10^{-8}$ atm×cm$^3$/s to $1\times10^{-7}$ atm×cm$^3$/s. Within the framework of the embodiments, the term "hermetically sealed" can mean, for example, that the barrier, here the housing, has a helium leak rate of less than $1\times10^{-7}$ atm×cm$^3$/s. In one embodiment, the helium leak rate can be less than $1\times10^{-8}$ atm×cm$^3$/s, in one embodiment less than $1\times10^{-9}$ atm×cm$^3$/s.

For the purpose of standardization, the above-mentioned helium leak rates can also be converted to the equivalent standard air leak rate. The definition of the equivalent standard air leak rate and conversion thereof are given in the standard ISO 3530. As a rule, because of the type of use of implantable electrical medical devices, the hermetic sealing properties and biocompatibility thereof are among their most important requirements. The implantable electrical medical device proposed here can, for example, be inserted into the body of a human or animal user, in one embodiment a patient. Because of this, the housing is generally exposed to a fluid of a body tissue. As a rule, therefore, it is important that body fluids do not penetrate into the housing and that fluids do not leak from said housing. In order to ensure this, the housing should be as impermeable as possible, in one embodiment with respect to body fluids.

Implantable Electrical Medical Device

In one embodiment, an implantable electrical medical device is a therapeutic device. In one embodiment implantable therapeutic device is implantable in the chest or the head, or both. In one embodiment, a therapeutic device is a defibrillator or a pacemaker or a combination of at least two of these devices. In one embodiment, a pacemaker is selected from the group composed of a cardiac pacemaker, a bladder pacemaker, an intestinal pacemaker, a brain pacemaker, a respiratory pacemaker and a diaphragmatic pacemaker or a combination of at least two of these devices. In one embodiment, a pacemaker is a cardiac pacemaker. In one embodiment, a cardiac pacemaker is a wireless cardiac pacemaker. In one embodiment, a therapeutic device is a cochlear implant.

In one embodiment, an implantable electrical medical device is a diagnostic device. In one embodiment, a diagnostic device is a biomonitor. In one embodiment, a biomonitor includes a device selected from the group composed of an EKG device, a Holter monitor, an event recorder, and a loop recorder, or a combination of at least two of these devices. In one embodiment, a EKG device is a long-term EKG device that stores data collected over a period of at least one hour. In one embodiment, a diagnostic device includes a transmission unit or a data storage unit or both. In one embodiment, a transmission device is configured for the wireless, telemetric transmission of data, EKG data. In one embodiment, a wireless transmission of data is transmission by means of waves In one embodiment, waves are longitudinal waves or transverse waves or both. In one embodiment, longitudinal waves are acoustic waves or sound waves or both. In one embodiment, transverse waves are electromagnetic waves. In one embodiment, electromagnetic waves are waves having the frequency of a mobile network or of Bluetooth or both. In one embodiment, a mobile network is a GSM network. Any unit for storing data that is considered by the person skilled in the art to be suitable for storing medical data, EKG data, in an implantable device can be selected as a data storage unit. In one embodiment, a data storage unit is a magnetic storage unit or a flash drive or both.

Meniscus

A meniscus is a curve in a surface of the third element, wherein the curve is caused by the interfacial tension of a liquid phase. In one embodiment, a liquid phase in this case is a melt. In one embodiment, a meniscus is a convex meniscus or a concave meniscus or both.

Composition

In one embodiment, a composition is a paste. In one embodiment, a paste is viscous. In one embodiment, a paste has a viscosity that is suitable for printing, screen printing. In one embodiment, a liquid contained in the composition is a vehicle.

Metal Particles of the Composition

In one embodiment, metal particles included in the composition are composed of one selected from the group consisting of Ag, Au, Cu, Pd, and Pt, or a combination of at least two thereof. The person skilled in the art knows that metal particles can have various shapes, surface configurations, sizes, specific surface areas, and specific surface area- or surface content-to-volume ratios. Many different possible shapes of metal particles are known to the person skilled in the art. For example, these include spherical, angular, rounded, elongated (rod-shaped and needle-shaped) and flat (planar) shapes. The metal particles may also include a mixture of particles of different shapes. Metal particles with a shape or a combination of shapes that promote sintering behavior, electrical contact, adhesion, and electrical conductivity are preferred in one embodiment. The metal particles have a length, width, and thickness. When the particle size is indicated, this refers to the length of the metal particles. The length of a particle is the length of the longest straight line that has a starting and end point on the surface of the particle. The width of the particle is the length of the longest straight line that has a starting and end point on the surface of the particle and is perpendicular to the length of the particle. The thickness of the particle is the length of the longest straight line that has a starting and end point on the surface of the particle and is perpendicular both to the length of the particle and to its width, in each case according to the above definition. In one embodiment, particles that are as uniform as possible are preferred. In this case, the ratios of length, width and thickness to one another are as close as possible to 1. These ratios are in one embodiment in the range of 0.7 to 1.5, in one embodiment 0.8 to 1.3, and in one embodiment 0.9 to 1.2. In this embodiment, for example, spherical or cubical shapes of the particles or combinations of both are preferred. In another embodiment, particles that are as non-uniform as possible are preferred. In this case, at least one of the ratios of length, width and thickness to one another is in one embodiment greater than 1.5, in one embodiment greater than 3, in one embodiment greater than 5. According to this embodiment, flake-shaped, rod-shaped, and needle-shaped metal particles or a combination of at least two of the above-mentioned metal particles or a combination with another metal particle shape are preferred. In one embodiment, preferred are also metal particles with surfaces that promote effective sintering as well as good electrical contact and high electrical conductivity.

Vehicles

In one embodiment, vehicles are inorganic and organic vehicles. In one embodiment, an inorganic vehicle is water. In one embodiment, an organic vehicle is a solution, an emulsion or a dispersion comprising one or a plurality of solvents. In this case, an organic solvent that ensures that the components of the composition are present in dispersed, emulsified or dissolved form is preferred. In one embodiment, organic vehicles promote optimum stability of the components in the composition and impart to the composition a viscosity that allows effective printing of the composition. In one embodiment, vehicles include the following as vehicle components:

(i) a binder, in one embodiment, in the range of 1 to 50 wt. %, in one embodiment 2 to 45 wt. %, and in one embodiment 3 to 40 wt. %;
(ii) a surfactant, in one embodiment in the range of 0 to 10 wt. %, in one embodiment 0 to 8 wt. %, and in one embodiment 0 to 6 wt. %;
(iii) one or at least two solvents, the amounts of which are determined according to the amounts of the other vehicle components;
(iv) optional additives, in one embodiment in the range of 0 to 10 wt. %, in one embodiment 0 to 8 wt. %, and in one embodiment 0 to 5 wt. %; wherein the figures in wt. % are based in each case on the total weight of the vehicle and sum up to 100 wt. %. According to one embodiment, preferred vehicles impart to the composition the maximum suitability for printing.

Binders

In one embodiment, binders are those that contribute towards obtaining a composition with suitable stability, suitability for printing, viscosity and sintering behavior. Binders are known to the person skilled in the art. All binders that are considered by the person skilled in the art as suitable for use according to one embodiment may be used as binders in the vehicle. In one embodiment, binders are resins. In one embodiment, binders are polymeric binders, monomeric binders and binders composed of a combination of polymers and monomers. Polymeric binders can also be copolymers, wherein at least two monomeric units are included in an individual molecule. In one embodiment, polymeric binders include a functional group in the main chain of the polymer, outside the main chain, or in the main chain and outside the main chain. In one embodiment, binders with a functional group in the main chain are polyesters, substituted polyesters, polycarbonates, substituted polycarbonates, polymers with a cyclic group in the main chain, polysugars, substituted polysugars, polyurethanes, substituted polyurethanes, polyamides, substituted polyamides, phenol resins, substituted phenol resins, copolymers of the monomers of one or a plurality of the above-mentioned polymers, optionally with other comonomers, or a combination of at least two of these. In one embodiment, polymers with a cyclic group in the main chain are polyvinyl butylates (PVB) and their derivatives and poly-terpineol and its derivatives, or mixtures thereof. In one embodiment, polysugars are cellulose and alkyl derivatives thereof, in one embodiment, methyl cellulose, ethyl cellulose, propyl cellulose, butyl cellulose, and their derivatives, and mixtures of at least two of these. In one embodiment, polymers with a functional group outside their main chain are those with an amide group, an acid group and/or an ester group (also referred to as acrylic resins), or polymers with a combination of the above-mentioned functional groups. In one embodiment, polymers with an amide group outside the main chain are polyvinylpyrrolidone (PVP) and its derivatives. In one embodiment, polymers with an acid group and/or an ester group outside the main chain are polyacrylic acid and its derivatives, polymethacrylate (PMA) and its derivatives, and polymethyl methacrylate (PMMA) and its derivatives, or combinations of at least two of these. In one embodiment, monomeric binders are ethylene glycol-based monomers, terpineol resins, and resin derivatives, or a combination of at least two of these. In one embodiment, ethylene glycol-based monomeric binders have an ether group, an ester group, or both. In one embodiment, ether groups are methyl, ethyl, propyl, butyl, pentyl, hexyl and higher alkyl ether groups. In one embodiment, ester groups are acetate and its alkyl derivatives, in one embodiment, ethylene glycol monobutyl ether monoacetate, or a mixture of the above-mentioned substances. In one embodiment, binders are alkyl cellulose, in one embodiment, ethyl cellulose, and their derivatives, and mixtures thereof with other binders selected from those mentioned above or others.

Surfactants

In one embodiment, surfactants are those that contribute towards obtaining a composition with suitable stability, suitability for printing, viscosity and sintering behavior. Surfactants are known to the person skilled in the art. All surfactants that are considered by the person skilled in the art to be suitable for use according to one embodiment can be used in the vehicle as surfactants. In one embodiment, surfactants are based on linear chains, branched chains, aromatic chains, fluorinated chains, siloxane chains, polyether chains, or combinations of at least two of these. In one embodiment, surfactants have single, double, or multiple chains. In one embodiment, surfactants have nonionic, anionic, cationic, or zwitterionic terminals. In one embodiment, surfactants are polymeric or monomeric or a mixture of both. In one embodiment, surfactants can have pigment affinic groups, in one embodiment, hydroxy functional carboxylic acid esters with pigment affinic groups (for example DISPERBYK®-108, manufactured by BYK USA, Inc.), acrylate copolymers with pigment affinic groups (for example DISPERBYK®-116, manufactured by BYK USA, Inc.), modified polyethers with pigment affinic groups (for example TEGO® DISPERS 655, manufactured by Evonik Tego Chemie GmbH), and other surfactants with groups having high pigment affinity (such as TEGO® DISPERS 662 C, manufactured by Evonik Tego Chemie GmbH). In one embodiment, other polymers are polyethylene glycol and its derivatives, alkyl carboxylic acid and its derivatives or salts, or mixtures of at least two of these. In one embodiment, polyethylene glycol is poly(ethylene glycol) acetic acid. In one embodiment, alkyl carboxylic acids are those with fully saturated or mono- or polyunsaturated alkyl chains or mixtures of at least two of these. In one embodiment, carboxylic acids with saturated alkyl chains are those with alkyl chain lengths in the range of 8 to 20 carbon atoms, in one embodiment, $C_9H_{19}COOH$ (capric acid), $C_{11}H_{23}COOH$ (lauric acid), $C_{13}H_{27}COOH$ (myristic acid), $C_{15}H_{31}COOH$ (palmitic acid), $C_{17}H_{35}COOH$ (stearic acid), or mixtures of at least two of these. In one embodiment, carboxylic acids with unsaturated alkyl chains are $C_{18}H_{34}O_2$ (oleic acid) and $C_{18}H_{32}O_2$ (linoleic acid).

Solvents

In one embodiment, solvents are those which, in method step f) or g) or in both of the method 1 according to the embodiments, can be removed from the composition to a significant portion. In one embodiment, in method step f) or g) or both, the percentage by weight of the solvent in the composition is reduced by 80%, in one embodiment 95%, based on the percentage by weight immediately prior to method step f). In one embodiment, solvents are those that contribute towards obtaining a composition having suitable stability, capacity for printing, viscosity, and sintering behavior and which lead to suitable electrical conductivity and electrical contact of the third element. Solvents are known to the person skilled in the art. All solvents that are considered by the person skilled in the art to be suitable for use according to one embodiment can be used as solvents in the vehicle. In one embodiment, solvents are used that make it possible to impart to the composition the best possible suitability for printing. In one embodiment, solvents are liquid at standard ambient temperature (298.15 K, 100 kPa). In one embodiment, solvents have a boiling temperature of over 90° C. or a melting temperature of over −20° C. or both. In one embodiment, solvents are polar or nonpolar, protic, aprotic, aromatic, non-aromatic, ionic, or a combination of at least two of these. In one embodiment, solvents are monoalcohols, dialcohols, polyalcohols, monoesters, diesters, polyesters, monoethers, diethers, polyethers, solvents comprising one or at least two functional groups of these categories, optionally containing functional groups of other categories, in one embodiment, cyclic groups, aromatic groups with unsaturated bonds, alcohol groups in which one or at least two oxygen atoms are replaced by heteroatoms, ether groups in which one or at least two oxygen atoms are replaced by heteroatoms, ester groups in which one or at least two oxygen atoms are replaced by heteroatoms, and mixtures of at least two of these. In one embodiment, esters are dialkyl esters of adipic acid, with in one embodiment, alkyl components being methyl, ethyl, propyl, butyl, pentyl, hexyl, and higher alkyl groups or mixtures of at least two of these, in one embodiment, dimethyl adipate, and mixtures of two or more adipate esters. In one embodiment, ethers are diethers, in one embodiment, dialkyl ethers of ethylene glycol, with in one embodiment, alkyl components being methyl, ethyl, propyl, butyl, pentyl, hexyl, and higher alkyl groups or mixtures of at least two of these, and mixtures of two diethers. In one embodiment, alcohols are primary, secondary, and tertiary alcohols or a mixture of two or more alcohols. In one embodiment, alcohol is terpineol and its derivatives. In one embodiment, alcohols comprising two or more functional groups are 2,2,4-trimethyl-1,3-pentane diol-mono-iso-butyrate, also referred to as texanol, and its derivatives, 2-(2-ethoxyethoxy)ethanol, also referred to as carbitol, alkyl derivatives thereof, in one embodiment, methyl, ethyl, propyl, butyl, pentyl, and hexyl carbitol, in one embodiment, hexyl carbitol or butyl carbitol, and acetate derivatives thereof, in one embodiment, butyl carbitol acetate, or mixtures of at least two of the above-mentioned substances.

Additives

In one embodiment, additives in the vehicle are different from the above-mentioned vehicle components and contribute towards preferred properties of the composition, such as suitable viscosity, sintering properties, electrical conductivity of the third element produced from the composition, and electrical contact. All additives that are considered by the person skilled in the art to be suitable for use according to one embodiment can be used as additives in the vehicle. In one embodiment, additives are thixotropic agents, viscosity regulators, stabilisers, inorganic additives, thickeners, emulsifiers, dispersants, and pH regulators. In one embodiment, thixotropic agents are carboxylic acid derivatives, in one embodiment, fatty acid derivatives. In one embodiment, a fatty acid derivatives are $C_9H_{19}COOH$ (capric acid), $C_{11}H_{23}COOH$ (lauric acid), $C_{13}H_{27}COOH$ (myristic acid), $C_{15}H_{31}COOH$ (palmitic acid), $C_{17}H_{35}COOH$ (stearic acid), $C_{18}H_{34}O_2$ (oleic acid) and $C_{18}H_{32}O_2$ (linoleic acid), or mixtures of at least two of these. In one embodiment, a mixture comprising fatty acid derivatives is castor oil.

Superimposing

The composition can be superimposed by any method that is considered suitable by the person skilled in the art for superimposing of the composition onto a contact surface according to one embodiment, with application to the contact surface being preferred. This includes but is not limited to impregnation, dipping, dripping, pouring, squirting, spraying, blade coating, pour-coating, painting, printing, or a combination of at least two of these methods. In one embodiment, printing methods are jet printing, silkscreen printing, pad printing, offset printing, relief printing, and screen printing or a combination of at least two of these. In one embodiment, printing, or screen printing is used.

Treatment/Disease/Dysfunction

In one embodiment, treatment is neurotherapy or cardiotherapy, or both. In this case, neurotherapy includes electrical stimulation of a nerve. In one embodiment, cardiotherapy includes electrical stimulation of a heart. In one embodiment, neurotherapy is one selected from the group composed of deep brain stimulation (DBS), spinal cord stimulation, vagus nerve stimulation, sacral nerve stimulation and gastric or intestinal nerve stimulation or a combination of at least two of these. In one embodiment, cardiotherapy is one selected from the group composed of cardiac pacemaker therapy, ICD therapy, CRT-P therapy and CRT-D treatment or a combination of at least two of these. In one embodiment, deep brain stimulation is a treatment for diseases selected from the group composed of Alzheimer's, Parkinson's disease, tremor, depression, epilepsy, dystonia, obsessive-compulsive disorder, Tourette's syndrome, coma and trauma or a combination of at least two of these. In one embodiment, spinal cord stimulation is a treatment for a disorder selected from the group composed of chronic back pain, post-discotomy syndrome, complex regional pain syndrome, and therapy-resistant pain, in one embodiment, due to ischemia, or a combination of at least two of these. In one embodiment, vagus nerve stimulation is a treatment for a disease selected from the group composed of epilepsy, depression and chronic heart failure (CHF) or a combination of at least two of these. In one embodiment, sacral nerve stimulation is a treatment for a disease selected from the group composed of urinary incontinence, urinary retention, frequent urge to void, fecal incontinence, idiopathic constipation, interstitial cystitis, and chronic anal fissure or a combination of at least two of these. In one embodiment, gastric or intestinal nerve stimulation is a treatment for obesity. In one embodiment, cardiac pacemaker therapy is a treatment for bradycardia or tachycardia or both. In one embodiment, ICD treatment is a treatment for atrial fibrillation or ventricular tachycardia or both. In one embodiment, CRT-P-treatment is a treatment for a chronic heart defect. In one embodiment, CRT-D treatment is a therapy for a heart-defect-induced conduction disorder or ventricular dyssynchrony or both.

Measurement Methods

The following measurement methods are used within the framework of one embodiment. Unless otherwise stated, the measurements were conducted at an ambient temperature of 25° C., an ambient atmospheric pressure of 100 kPa (0.986 atm), and a relative air humidity of 50%.

Biocompatibility

Biocompatibility is determined according to the standard 10993-4:2002.

Roughness

Roughness is determined according to the standard EN ISO 4288: 1997 as the mean roughness $R_a$ described therein.

Porosity

For measurement of porosity, metallographic grinding samples were first produced by embedding the samples in epoxide resin, grinding them with SiC paper having successively smaller grain size, and polishing them with a diamond paste. The outermost layer of each sample was removed by etching. After this, images of the sample surfaces treated in this manner were prepared using an optical microscope and an electron microscope. In this process, the purpose was to achieve the highest possible contrast between the pores of the sample and the material (metal and ceramic). In order to evaluate these images, the greyscale images were converted by the Otsu method into binary images. Specifically, the pixels of the images were each assigned by means of a threshold value to a pore or the sample material. After this, porosity was determined based on the binary images as the quotient of the number of pixels that constituted pores and the total number of pixels per image. Porosity was determined as the arithmetic mean of 5 images taken on 5 grinding samples respectively.

Bulk Density/True Density

The ratio of bulk density to true density is calculated by the formula porosity=1−(bulk density/true density). The bulk density is the actual density of the sample with pores. The true density is the density of the sample without pores.

Electrical Resistance of the Third Element/the Electrically Conductive Connection The electrical resistance was determined by four-line sensing. In the four-line sensing unit, a known electrical current flows through the resistor via two of the lines. The voltage drop across the resistor is detected with high impedance via two further lines and measured using a voltage measuring unit. The resistance to be measured is calculated based thereon according to Ohm's law as the quotient of voltage and current.

Metallographic Grinding Pattern

The sample is cut with a cooled separating saw equipped with a diamond disc such that the surface to be tested is exposed. The cut sample is placed in a receptacle filled with EpoFix (Struers GmbH) as an embedding material. The embedding material has been previously mixed according to the instructions for use. After hardening for 8 hours at room temperature, the sample can be further processed. First, the sample is ground with a Labopol-25 (Struers GmbH). Silicon carbide paper 180-800 (Struers GmbH) is used for grinding at 250 rpm. The sample is then polished with a Rotopol-2 equipped with Retroforce-4, MD Piano 220 and MD Allegro. The grinding pattern obtained is investigated using Zeiss Ultra 55 scanning electron microscope (Carl Zeiss AG) equipped with a field emission electrode at an acceleration voltage of 20 kV and a pressure of approx. $3\times10^{-6}$ mbar. In some cases, the grinding pattern was used to determine the elemental composition of the sample material. For this purpose, EDX (energy dispersive X-ray spectroscopy) measurement was carried out as a line scan. The Zeiss Ultra 55 with IncaPentaFETx3 and the software "The Microanalysis Suite Issue 18d+SP3" (both from Oxford Instruments), as well as an aperture of 30 μm, were used in this measurement.

Grain Size

Grain size is determined using a metallographic grinding pattern obtained by one of the above methods according to the line cutting method. In this case, line patterns are used, and the grain size is determined based on the average cutting length. The method is carried out according to EN 623-3: 2003. The grain size used herein is therefore the same as the mean grain size determined in the standard from the cutting line length. For measurement, the Zeiss Ultra 55 (Carl Zeiss AG) scanning electron microscope is again used. According to item 7.3 of the standard, microstructure images of 3 different areas of the sample are prepared for each measurement. Moreover, in cases where method A is applicable (see the standard for criteria), the procedure used is that of the first alternative under item 8.2 of the standard.

Pore Size

Pore size is determined using metallographic grinding patterns obtained by the above methods according to the line cutting method. In this case, line patterns are used, and the pore size is determined based on the average cutting length. The method is carried out analogously to the standard EN 623-3:2003 for grain sizes. In this case, the method described under item 8.3 is used with the evaluation according to item 9.2, wherein the pores are to be taken as the basis in each case.

Mass-Specific Surface Area

Mass-specific surface area is determined according to DIN ISO 9277:2003-05 by gas adsorption according to the BET method. Nitrogen is used as an adsorptive. In degassing, a control time period of 20 minutes during which the pressure does not change substantially is used. The saturation vapour pressure of the adsorptive is directly measured using a saturation vapour pressure thermometer. The gravimetric measuring method according to item 6.3.2 of the standard is used in compliance with the recommendations given. Equation (1) under item 7.1 is taken as a basis for evaluation. Multipoint determination according to item 7.2 is used. As recommended in the standard, the area requirement $a_m=0.162$ nm$^2$ is used for nitrogen at 77 K. Single point determination according to 7.3 is not used. A "Gemini 2360 Surface Area Analyzer" from Micromeritics GmbH (Rutherford 108, D-52072 Aachen) is used for measurement.

Distance Between the First and the Further Contact Surface

The distance between the first and the further contact surface is measured with an outside micrometer.

$D_{50}$ of the Metal Particles

Measurement of particle size ($D_{50}$) is carried out according to ISO 13317-3:2001. A Sedigraph 5100 with the software Win 5100 V2.03.01 (from Micromeritics) is used for the measurement. The device operates by means of x-ray irradiation and gravitational sedimentation. A sample of 400 to 600 mg of the metal particles to be measured is weighed out in a 50 ml beaker, and 40 ml of Sedisperse P11 (from Micromeritics, density approx. 0.74 to 0.76 g/cm$^3$, viscosity approx. 1.25 to 1.9 mPa·s) is added as a suspending agent in order to obtain a suspension. A magnetic stirring bar is added. The sample is homogenized with an Ultrasonic Sonifer 250 (from Branson) at power level 2 for 8 minutes. The sample is stirred with the magnetic stirrer. The sample preprocessed in this manner is placed in the measuring instrument, and measurement is begun. The temperature of the suspension is recorded, with the values typically being in the range of 24 to 45° C. The viscosity of the suspension measured at this temperature is used for calculation. The density (density of silver 10.5 g/cm$^3$) and the mass of the sample are used to determine particle size and indicate the $D_{50}$.

Halogen Content

The halogen content of the composition was determined according to the standard BS EN 14582.

Layer Thickness

A Hommel-Etamic Tester T8000 profilometer with the software Turbo-Wave V7.53 (both from Jenoptik) was used to measure layer thickness. The probe TKLT 300/17 is guided over the layer surface at a distance of 2.5 mm and a velocity 0.5 mm/s. The scan is carried out perpendicularly to the edge of the layer. 32 such scans were carried out, and the mean value was determined as a result thereof.

Viscosity

Viscosity measurements were carried out using a Thermo Fischer Scientific Corp. "Haake Rheostress 6000" with an MPC60 Ti bottom plate and a C 20/0.5° Ti cone plate, as well as the software "Haake RheoWin Job Manager 4.00.0003". After the distance zero point was set, a sample sufficient for measurement was placed on the bottom plate. The cone plate is moved into measurement position at a distance of 0.026 mm and excess sample material is removed with a spatula. The sample is temperature-controlled to 25° C., and rotation measurement is begun. The shear rate is increased from 0 to 20 s$^{-1}$ in 48 s at 24 equidistant measuring points and further to 150 s$^{-1}$ in 312 s at 156 equidistant measuring points. After a waiting period of 60 s at a shear rate of 150 s$^{-1}$, the shear rate is reduced from 150 s$^{-1}$ to 20 s$^{-1}$ in 312 s at 156 equidistant measuring points and further to 0 in 48 s at 24 equidistant measuring points. Microtorque correction, microstress control and moment of inertial control were activated. The measured viscosity is the value at the shear rate of 100 s$^{-1}$ during the reduction in shear rate.

Embodiments are presented in greater detail below by means of examples and drawings, wherein the examples and drawings are by no means to be interpreted as limiting the scope of the embodiment.

Figure 9:
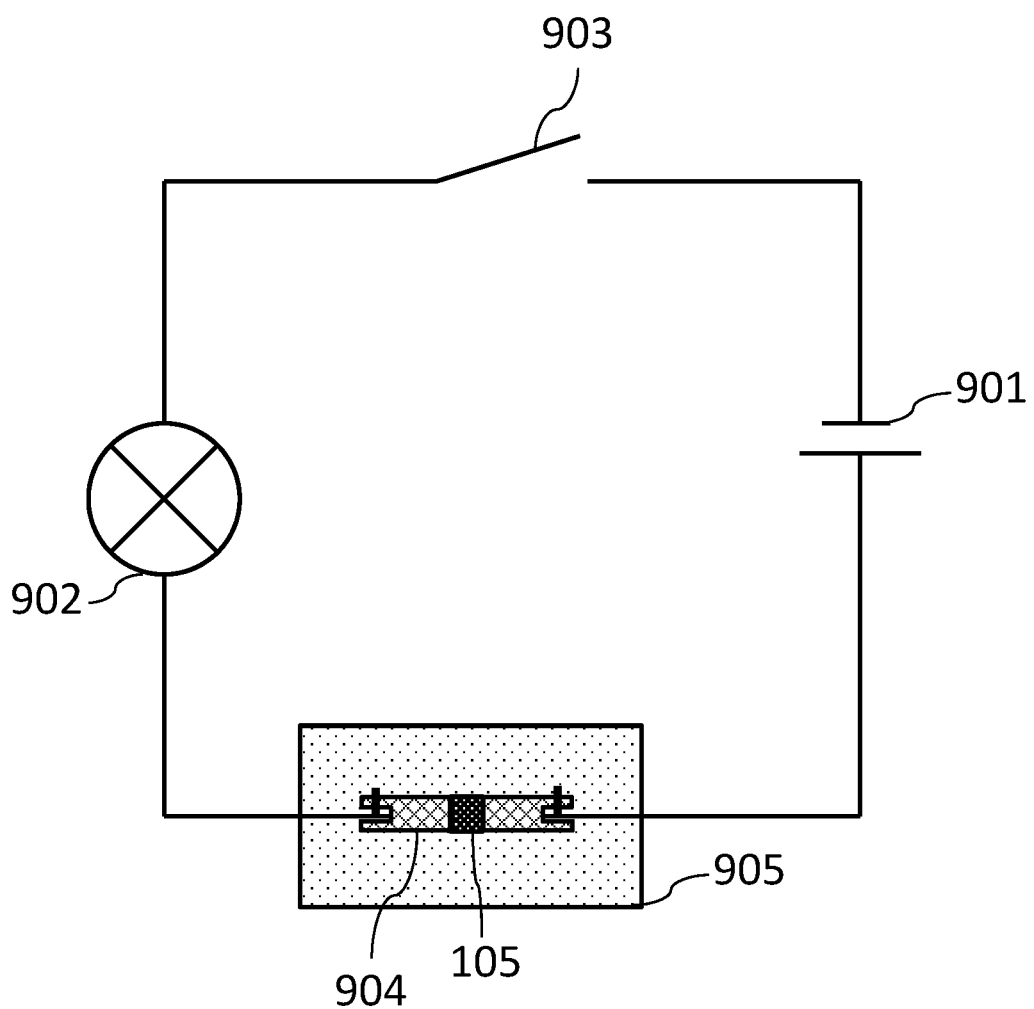
FIG. 9 is a schematic view of a measurement setup.

One circuit each according to FIG. 9 was constructed for the examples according to the embodiments and the examples not according to the embodiments. Each of the circuits included a 9 V 550 mAh-alkaline battery manufactured by Varta as a voltage source and a model 0816K009SR electromotor manufactured by Faulhaber as a consumer unit in the circuit. The battery was connected to the motor by means of a battery clip and cables. Moreover, each circuit contained a switch by means of which the circuit could be broken. In addition, one stripped cable end each was inserted into a blind borehole of one copper pin each and fixed in place using a transversely engaging screw. Each of the two copper pins was 10 mm long and had a diameter of 2 mm. The two front sides of the copper pins, depending on the example and comparative example, were electrically connected to each other by means of a soldered connection not according to one embodiment or a sintered connection according to one embodiment. In every case, the electrical connection had a diameter of 2 mm and a length of 2 mm. This was ensured by grinding in a post-processing step after production of the connection. Moreover, each of the copper pins together with the electrical connection was fixed to an electric vibrating table manufactured by FORM+TEST Seidner & Co. GmbH via a screw terminal.

In the examples and comparative examples, the circuit was closed with a switch so that the electric motor was operated in idling mode. At the same time, the vibrating table was activated at 3000 vibrations per minute. After vibration for 1 h, the vibrating table was turned off. If the electrical connection between the two copper pins came loose during vibration, causing the motor to shut down, this was counted as a breakdown. In the absence of a breakdown, the motor was operated until the voltage source failed. The duration of the motor running time was measured to determine the battery life. For the individual examples and comparative examples, the details on production of the electrical connection between the copper pins are given below. The porosity of the electrical connections produced was determined in each case by the measurement method given above after the measurement in the circuit. The following table gives the mean values for porosity over the 100 feedthroughs for each example and comparative example.

Example 1

First, 86 g of a metal powder produced by US Research Nanomaterials Inc. composed of Ag particles with a particle size of 30 to 50 nm was thoroughly mixed with 14 g of a polymer system in a Speedmixer kneader produced by Hauschild & Co KG for 10 minutes. The polymer system was composed of 10 wt. % of butyl diglycol, 68.77 wt. % of diethyl sebacate and 21.23 wt. % of Vitel 2700B from Bostik Inc. The paste obtained was fed through a 3-roller mill with stainless steel rollers until a homogeneous paste was obtained.

The homogeneous paste obtained in this manner was applied by means of screen printing to the respective front sides of both copper pins. In this process, a wet layer thickness of 25 μm was achieved. After this, the applied paste was dried for 15 minutes at 80° C. Moreover the copper pins provided with the dried paste were installed in a uniaxial press such that the copper pins could be electrically connected to each other by means of the paste by uniaxial pressing. Uniaxial pressing was carried out at 250° C. for a holding period of 30 minutes with a contact pressure of 20 MPa under argon inert gas. After this, each of the copper pins was installed in the circuit by inserting stripped cable ends into bores in the free front sides and fixing the cable ends using screws.

Example 2

In example 2, we proceeded as in example 1, with the paste being applied by dispensing to the front sides of the copper pins. In this process, a wet layer thickness of 35 μm was achieved. Moreover, uniaxial pressing was carried out at 300° C. for a holding time of 5 minutes. After pressing, the electrical connection was also sintered under an argon gas atmosphere at 300° C. for a holding time of 30 minutes. The heating rate was 50 K/min.

Comparative Example 1

In comparative example 1, the electrical connection between the two copper pins was produced by soldering of a silver disc with a thickness of 30 μm and a diameter of 2.0 mm. The soldering was carried out in a vacuum, with a soldering temperature of 980° C. being maintained for 3 min.

Comparative Example 2

In comparative example 2, a soldering paste Indium 9.72 manufactured by Indium Corporation was applied by dispensing to the copper pins and then soldered according to the manufacturer's instructions.
Evaluation

|  | Example 1 | Example 2 | Comparative example 1 | Comparative example 2 |
|---|---|---|---|---|
| Porosity of electrical connection | 0.1 | 0.13 | 0 | 0 |

For each example and comparative example, 100 electrical connections respectively were produced as described above and tested according to the above method. This means that a breakdown rate was determined for each example according to one embodiment and each example not according to one embodiment. Moreover, mean battery life was determined from the test runs without breakdowns. This yielded a ratio of the mean value of the breakdown rates in the examples according to one embodiment to the mean value of the breakdown rates in the comparative examples not according to one embodiment of 1:1.8. Moreover, based on the examples and comparative examples with no breakdowns, a ratio was calculated of the mean battery lives of the examples according to one embodiment to those of the comparison examples not according to one embodiment of 1:0.65. Accordingly, the electrical connections according to one embodiment showed a lower breakdown rate and longer battery life than the soldered connections not according to one embodiment.

FIG. 1a illustrates a schematic view of an apparatus according to one embodiment 100. The apparatus 100 includes a first frame 101, a further frame 102, a first element 103, a second element 104 and a third element 105. The first frame 101 is a flange. The flange is composed of titanium. The further frame 102 is a feedthrough sleeve and is composed of an electrically insulating ceramic ($Al_2O_3$). The feedthrough sleeve is soldered into the flange with a gold solder. This means that the first frame 101 frames the further frame 102. The first element 103, a connecting pin, is also soldered into the feedthrough sleeve with a gold solder. This means that the further frame 102 frames the first element 103. In addition, the feedthrough sleeve electrically insulates the connecting pin from the flange. The connecting pin is composed of a platinum-iridium alloy. The second element 104, here an electrically conductive cable, is connected in an electrically conductive manner to the third element 105 and the connecting pin. This connection was established by means of a sintering process in which the third element 105 was obtained. The third element 105 has a porosity of 0.1. The third element 105 is composed of platinum to 99 wt. % based on the third element 105.

Figure 1B:
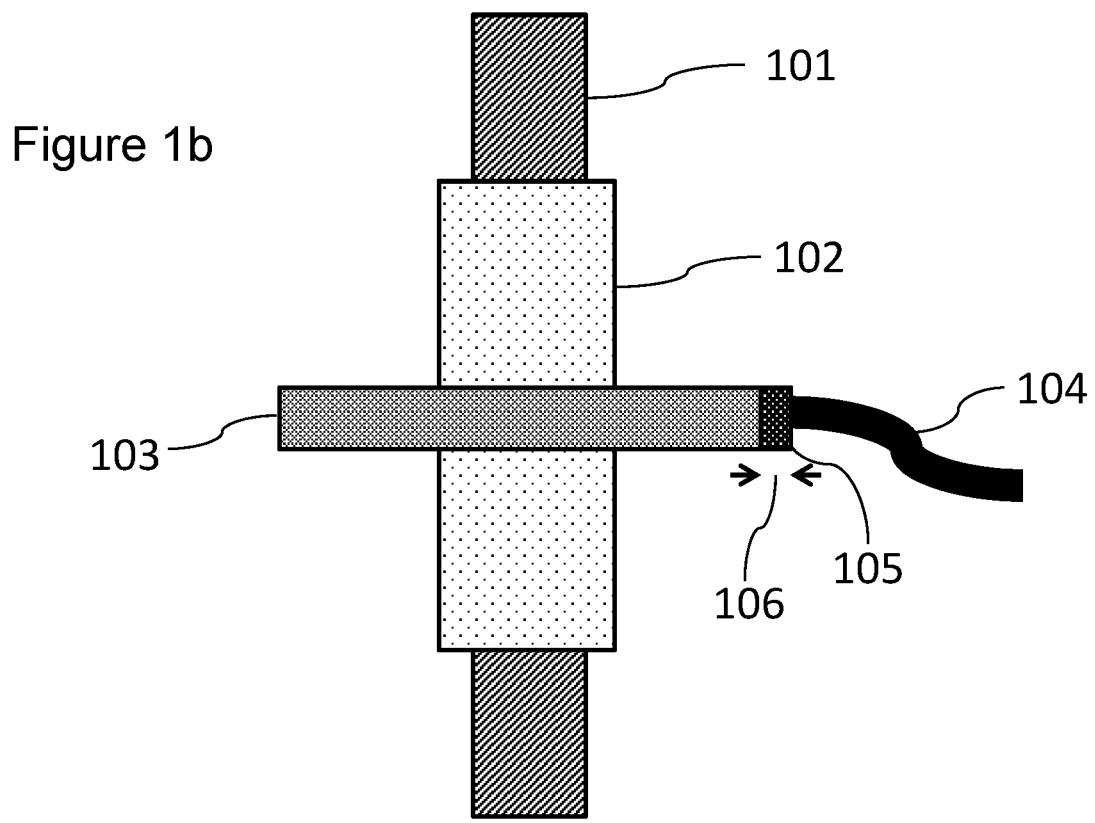

FIG. 1b illustrates a schematic sectional view of the apparatus according to one embodiment 100 in FIG. 1a. In addition to FIG. 1a, FIG. 1b illustrates a layer thickness 106 of the third element 105. This means that the third element 105 forms a layer that is superimposed onto the connecting pin.

Figure 2:
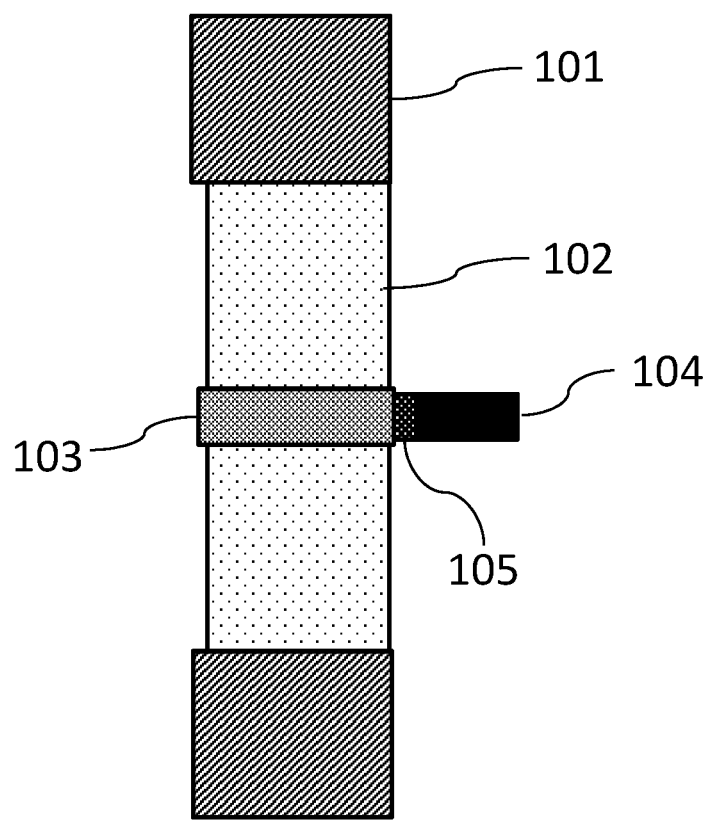
FIG. 2 is a schematic sectional view of a further apparatus according to one embodiment.

FIG. 2 illustrates a schematic sectional view of a further apparatus according to one embodiment 100. The apparatus 100 includes a first frame 101, a further frame 102, a first element 103, a second element 104 and a third element 105. The first frame 101 is a flange. The flange is composed of titanium. The further frame 102 is a ring of a ceramic ($Al_2O_3$). The further frame 102 is soldered into the flange with a gold solder. A ring opening of the ring is penetrated by the first element 103, a connecting pin. The first element 103 is composed of an electrically conductive cermet. The first element 103 and the further frame 102 have been obtained as a single piece in a sintering process. The second element 104 is a pin for electrical contacting of a circuit board. The third element 105 connects the pin to the connecting pin in an electrically conductive manner. This connection was established by means of a sintering process in which the third element 105 was obtained. The third element 105 has a porosity of 0.1. The electrical connection has a resistance of 0.1 mΩ. Moreover, the third element 105 includes no meniscus. The third element 105 is composed of 99.5 wt. % of silver based on said third element 105.

Figure 3:
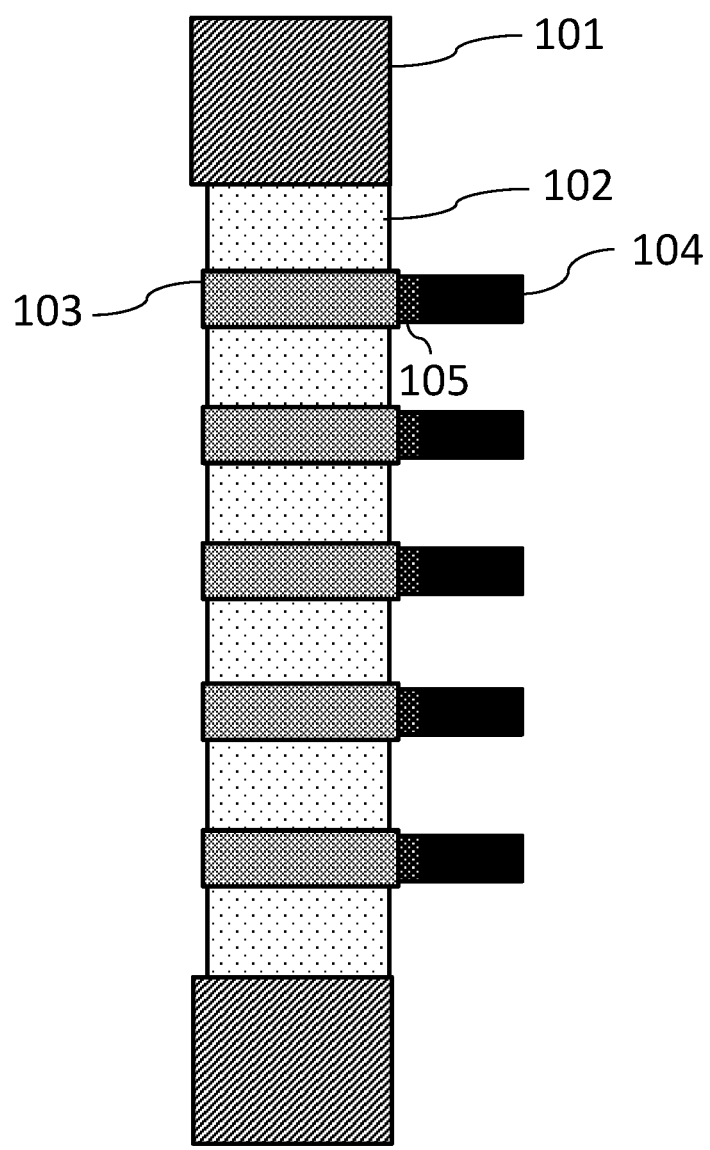
FIG. 3 is a schematic sectional view of a further apparatus according to one embodiment.

FIG. 3 illustrates a schematic sectional view of a further apparatus according to one embodiment 100. The apparatus 100 includes a first frame 101, a further frame 102, a first element 103, a second element 104 and a third element 105. The first frame 101 is a flange. The flange is composed of titanium. The further frame 102 is a perforated plate composed of a ceramic ($Al_2O_3$). The further frame 102 is soldered into the flange with a gold solder. A hole in the perforated plate is penetrated by the first element 103, a connecting pin. The first element 103 is composed of an electrically conductive cermet. The first element 103 and the further frame 102 have been obtained in one piece in a sintering process. The second element 104 is a pin for electrical contacting of a circuit board. The third element 105 connects the pin to the connecting pin in an electrically conductive manner. This connection was established by means of a sintering process in which the third element 105 was obtained. The third element 105 has a porosity of 0.1. The electrical connection has a resistance of 0.1 mΩ. Moreover, the third element 105 includes no meniscus. The third element 105 is composed of 99.5 wt. % silver based on said third element 105. The apparatus 100 also includes a plurality of further connecting pins, further third elements 105 and further pins. Each further third element 105 electrically connects a further connecting pin to a further pin. Each further third element has a porosity in the range of 0.05 to 0.15.

Figure 4:
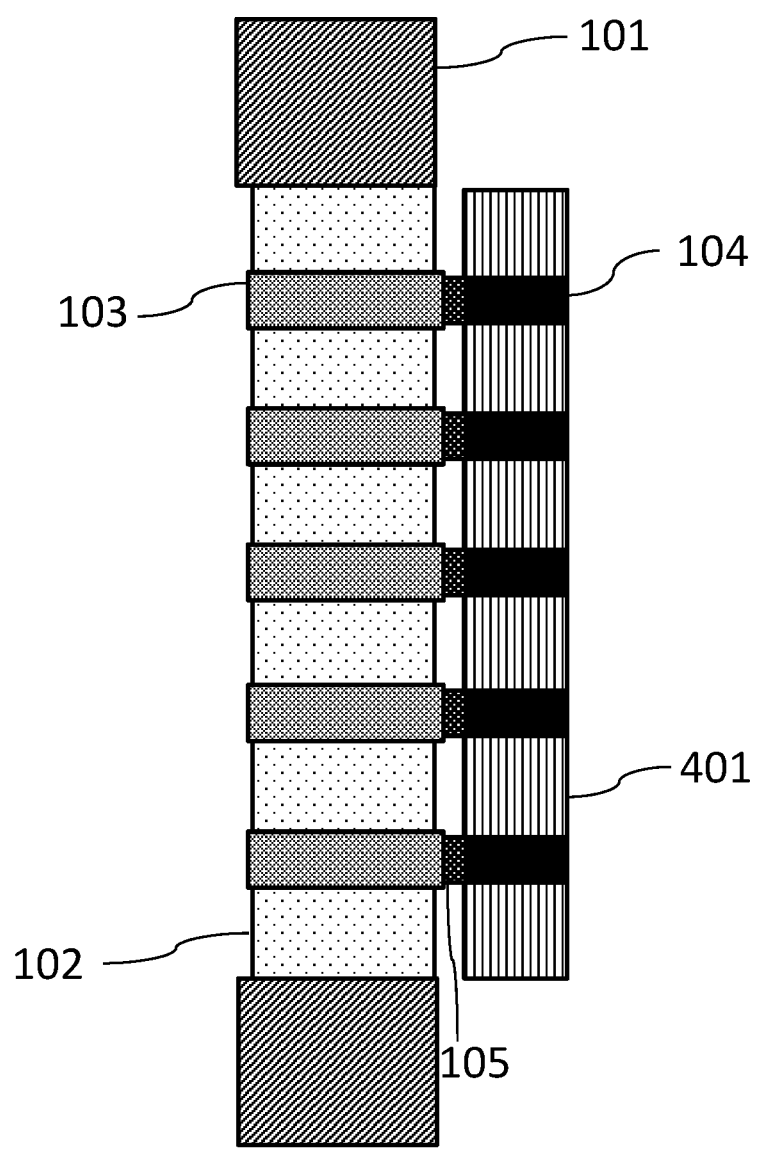
FIG. 4 is a schematic sectional view of a further apparatus according to one embodiment.

FIG. 4 illustrates a schematic sectional view of a further apparatus according to one embodiment 100. This apparatus 100 is the apparatus in FIG. 3, wherein each of the pins is connected to an MLCC filter 401. The MLCC filter 401 reduces the transmission of electrical interfering signals from the connecting pins and the pins to an electronic circuit connected to the pins.

Figure 5:
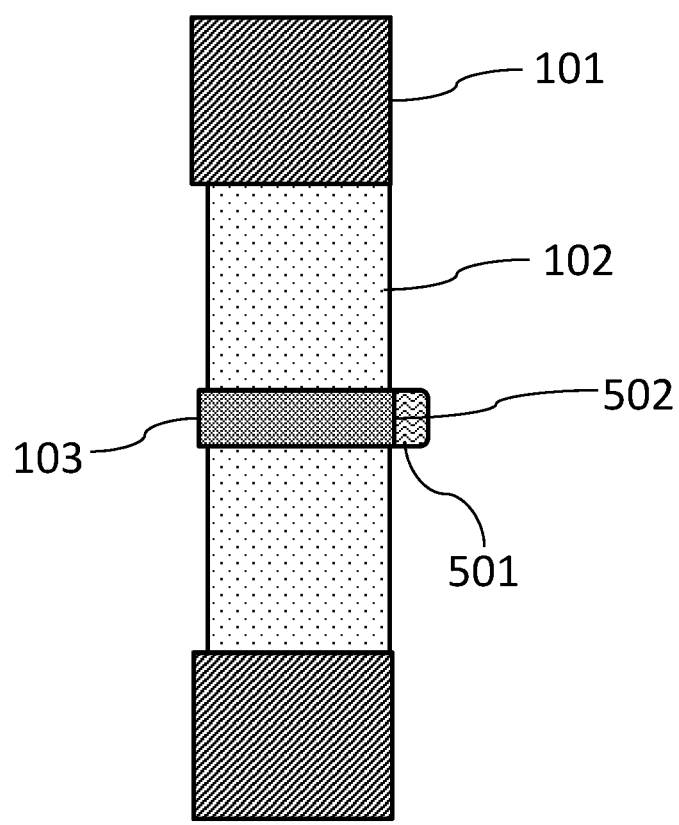
FIG. 5 is a schematic sectional view of an apparatus precursor according to one embodiment.

FIG. 5 illustrates a schematic sectional view of an apparatus precursor according to one embodiment 500. The apparatus precursor 500 includes a first frame 101, a further frame 102, and a first element 103. The first frame 101 is a flange. The flange is composed of titanium. The further frame 102 is a ring composed of a ceramic ($Al_2O_3$). The further frame 102 is soldered into the flange with a gold solder. A ring opening of the ring is penetrated by the first element 103, a connecting pin. The first element 103 is composed of an electrically conductive cermet. The first element 103 and the further frame 102 have been obtained in one piece in a sintering process. The connecting pin contains a first contact surface 502. A composition 501 is applied to this first contact surface 502. The composition 501 is a paste comprising a binder, a solvent and a plurality of metal particles. The metal particles are gold particles. The paste contains the gold particles in an amount of 90 wt. % based on the weight of said paste.

Figure 6:
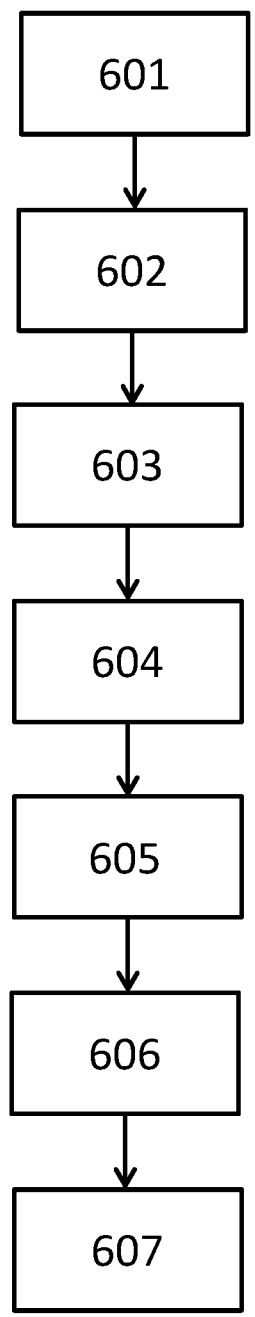
FIG. 6 is a flow diagram of a method according to one embodiment.

FIG. 6 illustrates a flow diagram of a method according to one embodiment 600. The method 600 includes method steps a) 601 to g) 607. In method step a) 601, a feedthrough is provided. The feedthrough includes a first frame 101, a further frame 102, and a first element 103. The first frame 101 is a flange. The flange is composed of titanium. The further frame 102 is a ring composed of a ceramic ($Al_2O_3$). The further frame 102 is soldered into the flange with a gold solder. A ring opening of the ring is penetrated by the first element 103, a connecting pin. The first element 103 is composed of an electrically conductive cermet. The first element 103 and the further frame 102 have been obtained in one piece in a sintering process. In method step b) 602, a second element 104 comprising a first contact surface is provided. The second element 102 is an electrical cable comprising a further contact surface. The further contact surface is a front side of a cable end. In method step c) 603, a composition 501 is provided. The composition 501 is a paste comprising a binder and a plurality of metal particles. The metal particles are silver particles. The paste includes the silver particles in an amount of 90 wt. % based on the weight of the paste. In method step d) 604, the paste is printed onto the first contact surface 502 in a screen printing process. In method step e) 605, the cable is brought into contact with the paste via its further contact surface, and the first contact surface 502 is thus connected to the further contact surface. In method step f) 606, the paste is thermally debinded. For this purpose, the paste is heated to 100° C. for 10 minutes. An element precursor, a green part, is obtained. In method step g) 607, the green part is sintered. For this purpose, the green part is heated to a temperature of 300° C. for 2 minutes. In this case, a mechanical pressure of 20 MPa is exerted on the green part. During sintering, the green part is in air. A third element 105 is obtained by means of this sintering.

Figure 7:
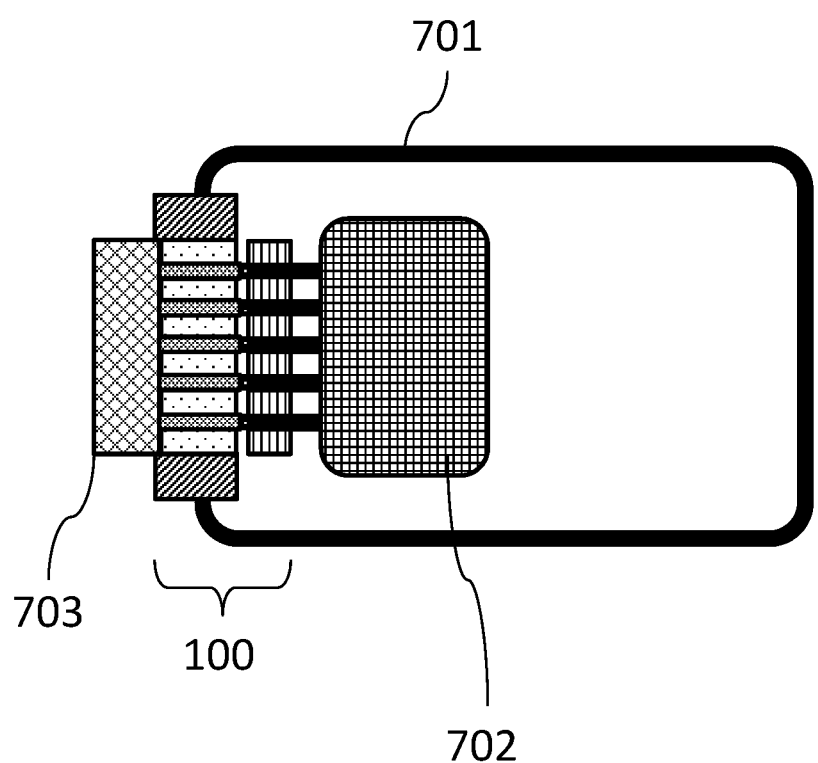
FIG. 7 is a schematic sectional view of an implantable electrical medical device according to one embodiment.

FIG. 7 illustrates a schematic sectional view of an implantable electrical medical device 700 according to one embodiment. The implantable electrical medical device 700 is a cardiac pacemaker. The cardiac pacemaker includes a housing 701 of titanium, control electronics 702 housed therein, and the apparatus according to one embodiment 100 of FIG. 4, welded into a housing opening in a hermetically sealed manner. In this process, the pins electrically connect the connecting pins and the control electronics 702 to one another. A header block 703 is attached on an outer side of the connecting pins.

Figure 8:
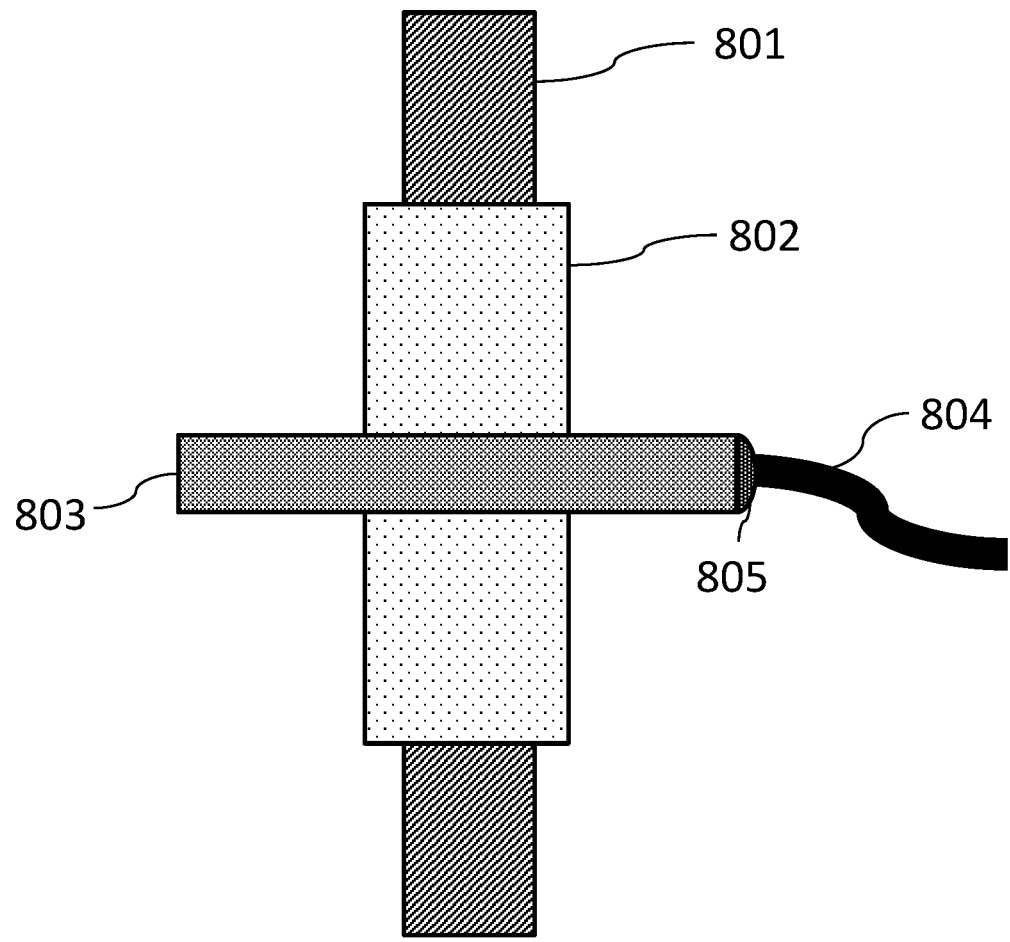
FIG. 8 is a schematic sectional view of a feedthrough contacted not according to one embodiment.

FIG. 8 illustrates a schematic sectional view of a feedthrough 800 contacted not according to one embodiment. The feedthrough 800 includes a flange 801, a feedthrough sleeve 802 soldered therein, and a connecting pin 803 soldered therein. The connecting pin 803 is soldered at one end via a soldered connection 805 to a cable 804. The soldered connection 805 includes a meniscus 805 that formed during soldering due to the interfacial tension of a liquid solder and which became part of the solid soldered connection 805 when the solder solidified.

FIG. 9 illustrates a schematic view of a measurement setup 900 for measuring the breakdown rate of the electrical connections and the battery life in the examples. Illustrated is a circuit comprising a voltage source 901, a consumer unit 902 and a switch 903. Moreover, the circuit includes two copper pins 904, each having a borehole in the longitudinal direction of the respective copper pin 904. A stripped cable end of the circuit is inserted into each borehole and fixed in place with a screw. Moreover, the free front sides of the copper pins 904 are connected to each other by means of the electrical connection to be tested. In the examples according to one embodiment, this is a sintered connection of the housing opening according to the third element 105 of one embodiment. Moreover, the two copper pins 904 with the electrical connection are fixed to a vibrating table 905 for measurement of the breakdown rate.

Although specific embodiments have been illustrated and described herein, it will be appreciated by those of ordinary skill in the art that a variety of alternate and/or equivalent implementations may be substituted for the specific embodiments shown and described without departing from the scope of the present embodiments. This application is intended to cover any adaptations or variations of the specific embodiments discussed herein. Therefore, it is intended that these embodiments be limited only by the claims and the equivalents thereof.

What is claimed is:

1. An apparatus comprising a first frame, a further frame, a first element, a second element and a third element;
    wherein
    a) the first frame frames the further frame;
    b) the further frame
        i) frames the first element, and
        ii) electrically insulates the first element and the first frame from each other;
    c) the first element is electrically conductive;
    d) the second element is electrically conductive;
    e) the third element
        i) provides an electrically conductive connection between the first element and the second element, and
        ii) has a porosity in the range of 0.13 to 0.2;
        iii) comprises Ag in an amount in the range of 10 to 100 wt. % based on the weight of the third element; and
        iv) has a layer thickness in the range of 0.2 to 0.6 mm.

2. The apparatus of claim 1, wherein the first element comprises a cermet.

3. The apparatus of claim 1, wherein the further frame comprises a ceramic.

4. The apparatus of claim 1, wherein the further frame and the first element are configured in one piece.

5. The apparatus of claim 1, wherein the second element is selected from the group composed of an electrical contact, a conductive path, a wire, a socket, and a plug, or a combination of at least two of these devices.

6. The apparatus of claim 1, wherein the apparatus further comprises an electrotechnical filter and wherein the first element or the second element or both is connected to the electrotechnical filter.

7. The apparatus of claim 1, wherein the third element has a porosity in the range of 0.13 to 0.16.

8. An implantable electrical medical device comprising a housing and the apparatus of claim 1;
   wherein the housing comprises a housing opening;
   wherein the first frame has been fitted into the housing opening.

9. A method for producing an implantable electrical medical device comprising a housing comprising a housing opening, wherein the method comprises a method step of inserting the apparatus of claim 1 into the housing opening such that the housing opening contains the first frame.

\* \* \* \* \*